United States Patent
Patil et al.

(12) United States Patent (10) Patent No.: US 12,419,828 B2
(45) Date of Patent: Sep. 23, 2025

(54) DENTAL CARE AND CLEANSING COMPOSITION

(71) Applicants: GROUP PHARMACEUTICALS LIMITED, Bengaluru (IN); Ratnadeep Patil, Mumbai (IN)

(72) Inventors: Ratnadeep Patil, Mumbai (IN); Ann Attavar, Bengaluru (IN); Laxmikant Sugandhi, Bengaluru (IN); Rajesh Kapoor, Bengaluru (IN)

(*) Notice: Subject to any disclaimer, the term of this patent is extended or adjusted under 35 U.S.C. 154(b) by 333 days.

(21) Appl. No.: 17/767,071

(22) PCT Filed: Jan. 27, 2021

(86) PCT No.: PCT/IN2021/050081
§ 371 (c)(1),
(2) Date: Apr. 7, 2022

(87) PCT Pub. No.: WO2021/152624
PCT Pub. Date: Aug. 5, 2021

(65) Prior Publication Data
US 2022/0362140 A1    Nov. 17, 2022

(30) Foreign Application Priority Data
Jan. 29, 2020 (IN) .............................. 2020 41003881

(51) Int. Cl.
*A61K 8/9789* (2017.01)
*A61K 8/04* (2006.01)
(Continued)

(52) U.S. Cl.
CPC ............ *A61K 8/9789* (2017.08); *A61K 8/042* (2013.01); *A61K 8/22* (2013.01); *A61K 8/988* (2013.01);
(Continued)

(58) Field of Classification Search
None
See application file for complete search history.

(56) References Cited

U.S. PATENT DOCUMENTS 4,069,312 A * 1/1978 Mannara .................. A61K 8/19
424/49
4,603,045 A * 7/1986 Smigel ..................... A61K 8/22
424/53
(Continued)

OTHER PUBLICATIONS

Jain et al, In vitro activity of ethanolic and water extract of guava leaves at various concentrations against Lactobacillus acidophilus Journal of Indian Association of Public Health Dentistry, vol. 12, issue 3, Jul.-Sep. 2014, p. 232-236 (Year: 2014).*
(Continued)

*Primary Examiner* — Lakshmi S Channavajjala
(74) *Attorney, Agent, or Firm* — Mainline Intellectual Property; Syam Anand (57) ABSTRACT

The present invention discloses a novel dental care composition comprising combination of various ingredients majorly includes natural ingredients which acts synergistically to treat various dental related disorders. The natural ingredients herein includes a synergistic composition of guava leaf extract, sodium perborate and honey. The said composition exhibits anti-oxidant, anti-microbial, anti-inflammatory and anti-septic properties.

4 Claims, 6 Drawing Sheets

(51) Int. Cl.
*A61K 8/22* (2006.01)
*A61K 8/98* (2006.01)
*A61Q 11/00* (2006.01)

(52) U.S. Cl.
CPC ........ *A61Q 11/00* (2013.01); *A61K 2800/522* (2013.01)

(56) References Cited

U.S. PATENT DOCUMENTS 6,171,604 B1 * 1/2001 Mousa .................... C08K 9/02 514/23
10,835,455 B2 * 11/2020 Payne ..................... A61K 8/19

OTHER PUBLICATIONS

Atwa et al. Effect of honey in preventing gingivitis and dental caries in patients undergoing orthodontic treatment. The Saudi dental Journal, 2014, 26:108-114. (Year: 2014).*

* cited by examiner

DENTAL CARE AND CLEANSING COMPOSITION

INTRODUCTION

The present invention relates generally to a novel dental cleansing composition wherein the composition comprising natural ingredients are synergistically activated by conventional chemical reactions to provide complete cleansing and tooth protection properties.

BACKGROUND

Typically, dental cleansing compositions provide two important functions basically, tooth cleansing functions and/or cosmetic function such as tooth whitening. Presently available cleansing formulations include a mixture of glycerine, alumina and sea salt such as in EP327776 B1 or a mixture with calcium salt as in U.S. Pat. No. 5,843,406. One other patent application U.S. Pat. No. 4,826,676 relates to a soluble fluoride ions based polishing agent and zinc-exchanged zeolite in the inhibition of the formation of plaque and tartar.

Furthermore, cosmetic properties such as skin whitening such as by gels, pastes, or liquids, including toothpastes that are mechanically agitated at the stained tooth surface to remove the stains, or by use of gels, pastes, or liquids that accomplish the tooth-bleaching effect by a chemical process while in contact with the stained tooth surface for a specified period, after which the formulation is removed. Few formulations include both wherein the mechanical process is followed by an auxiliary chemical process which may be oxidative or enzymatic.

The majority of professionally-monitored at-home tooth-bleaching compositions act by oxidation. These compositions are dispensed directly to a patient for use in a custom-made tooth-bleaching tray, held in place in the mouth for contact times of greater than about 60 minutes, and sometimes as long as 8 to 12 hours. The slow rate of bleaching is in large part, the consequence of formulations that are developed to maintain stability of the oxidizing composition. The most commonly used oxidative compositions contain the hydrogen peroxide precursor carbamide peroxide which is mixed with an anhydrous or low-water content, hygroscopic viscous carrier containing glycerine and/or propylene glycol and/or polyethylene glycol. When contacted by water, carbamide peroxide dissociates into urea and hydrogen peroxide.

Some of the present composition provides both tooth cleansing and cosmetic properties together, so to avoid repeated use of chemicals and reduces the effort and time of the user. However, it may be noted that the associated use of these composition with the slow rate of bleaching in the hygroscopic carrier, the presently available tooth-bleaching compositions cause tooth sensitization in over 50% of patients. Moreover, they are not formulated to address the needs of the oral cavity which not only has the presence of natural teeth and gums but also presence of filling materials, caps, dental implants, dentures made from various metals and materials such as ceramics etc that can cause varying oxidative stress point in the oral cavity.

Furthermore, the present formulations do not address the need for oral protective properties in dental care compositions. The oral cavity is constantly being subjected to bombardment from food and drinks including alcohol, tobacco products and nicotine in addition to the above said dental implants. As the oral tissue is very delicate, they are especially vulnerable to cell damage caused by free radicals and oxidative stress. The oral cavity is subjected to various unhealthy food habits which induces frequent changes in the acidic levels of the oral cavity.

Research indicates, that the periodontal microflora promotes events that lead to an increase in intracellular production of Physiological Reactive Oxygen Species (ROS). These species are formed as a result of normal oxygen metabolism and play an important role in cell signalling and homeostasis. However, during inflammation, ROS levels dramatically increase which result in the increase of oxidising conditions thus leading to cell structure. A study of dental plaque bacteria has implicated its role in inducing "Oxygen shock" to activate free radicals and the collagen-destroying enzymes. Habits such as tobacco chewing, alcohol abuse and smoking further increases oxidative stress.

Further research indicates human saliva provides a natural antioxidant element that help protect against oral diseases including cancer and are vital to tissue health and healing. Increase use of medications especially in adults leads to reduced salivary output leading to dryness of mouth depleting the reparative properties of saliva. However, in aerobic organisms this imbalance between the ROS generation and antioxidant levels leads to increased oxidative stress and cellular degeneration.

Recent research such as the review article "ROS Function in Redox Signaling and Oxidative Stress" indicate that ROS (Reactive Oxygen Species) are not just molecules that invoke cell damage, but it is now understood that they play a significant role in normal physiological and biological responses (i.e. redox biology). Hence there is an increasing need for dental care compositions address this balance and that is simple and natural in its interactions such that they do not produce more harm to the natural dental architecture.

Furthermore, it is need in art to use a natural oral care composition that provides a synergistic treatment properties such as anti-oxidant property, anti-inflammatory property, anti-microbial property and antiseptic property from natural compositions that are environmental friendly and safe for long term human use.

SUMMARY OF THE INVENTION

The following presents a simplified summary of one or more embodiments in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The present invention relates to a novel dental care composition that combines the benefit of anti-oxidants with the benefits of anti-inflammatory, astringent and anti-septic action. The said composition helps in the reduction of oxidative stress witnessed in the oral cavity along with the reducing inflammation of oral soft tissues particularly of the gums. Further, the present invention relates to a synergistic composition comprising of an unique combination of an anti-oxidant, an anti-microbial agent and an oxidising agent. The present invention synergistically interacts with one another and provides both the antibacterial, astringent and tissue protective properties of the oral cavity. The particular combination as disclosed in the invention includes guava extract, honey and sodium perborate. Further, the dental care compositions as disclosed in the present invention are free of chemical based anti-septic agents such as sodium hypochlorite, chlorhexidine and EDTA.

BRIEF DESCRIPTION OF THE DRAWINGS

For a more complete understanding of the present invention and the advantages thereof, reference is now made to the following descriptions taken in conjunction with the accompanying drawings wherein like numbers designate like objects and in which.

Persons skilled in the art will appreciate that elements in the figures are illustrated for simplicity and clarity and may have not been drawn to scale. For example the dimensions of some of the elements in the figure may be exaggerated relative to other elements to help to improve understanding of various exemplary embodiments of the present disclosure. Throughout the drawings it should be noted that like reference numbers are used to depict the same or similar elements features and structures.

DESCRIPTION OF THE INVENTION

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the detailed description of the invention below it may be advantageous to set forth definitions of certain words and phrases used throughout this patent document: the terms "include" and "comprise" as well as derivatives thereof mean inclusion without limitation; the term "or" is inclusive meaning and/or; the phrases "associated with" and "associated therewith" as well as derivatives thereof may mean to include be included within interconnect with contain be contained within connect to or with couple to or with be communicable with cooperate with interleave juxtapose be proximate to be bound to or with have a property of or the like; and the term.

Definitions

The term "synergy" herein refers to cumulative effect of combination of the ingredients in terms of an activity. For example, an activity of combination of 1X+1Y+1Z is and greater than X, Y or Z and greater than 2X, 2Y or 2Z acting independently. Here, X, Y, Z indicates various ingredients.

The term "synergistic composition" herein refers to cumulative effect of combination of the ingredients in terms of its independent activity (property) and synergistically acting as a catalyst imparting improved activity (property) to the composition.

Description of the Embodiments

In one embodiment, the present invention provides a unique synergistic oral care composition, that address the balance of ROS (Reactive Oxygen Species) in oral cavity, to reduce oxidative stress that cause cell damage and facilitate REDOX biology that is required for normal physiological functioning of the cells in the oral environment.

In one embodiment, the present invention relates to a novel dental care composition that combines the actions of an anti-oxidant, an anti-microbial agent and an oxidising agent, wherein the said composition provides both tissue protection of sensitive oral tissue and the prevention of further infection in the oral cavity.

In one embodiment, the anti-oxidant agent of the novel composition is the leaf extract of guava. The guava leaf extract is rich in phenolic compounds with folic acid and Vitamin C and acts as a rich source of anti-oxidant. The phenolic composition of Guava provides higher anti-inflammatory property of the oral wounds. Guava leaf extract acts as an effective free radical scavenger preventing the cellular damage by the inactivation of free radicals generated by metabolism, inflammatory process, dissimilar metals and other dental procedures etc.

In the above said embodiment, the phenolic components present in the guava leaf extract contain anti-inflammatory properties.

The said guava leaf extract acting as the anti-oxidant source that further cause the degradation of mineral deposits such as the bacterial plaque composed on calcium carbonate and converts the same into calcium bicarbonate enabling the same to be soluble with water. Furthermore, the said guava leaf extract prevent the formation of dental stains that occur from oxidation of organic and inorganic compounds in the oral cavity. In one embodiment, the said guava leaf extract is administered in such concentration as to achieve effective anti-oxidant property to the said composition.

In the above mentioned embodiments, the concentration of guava leaf extract in the composition is in the range of about 5% to about 15% or in other words the concentration of the extract includes at least 5%, at least 6%, at least 7%, at least 8%, at least 9%, at least 10%, at least 11%, at least 12%, at least 13%, at least 14% and at least 15% but not exceeding greater than 15%.

In yet another embodiment, the oxidising agent of the novel composition is perborates of sodium, a peroxide based oxidising agent. Sodium perborate acts as an active source of oxygen for cellular metabolism and further hydrolysis to produce hydrogen peroxide and borate. The said borate loosens the debris, removes stains and acts against obligate anaerobes. Furthermore, optimum production of hydrogen peroxide produced by sodium borate, as oxidising agent in the present composition provides the anti-septic and anti-inflammatory properties. Sodium perboarate is in general used in 3% to 5% concentrations disinfectant wherein at this moderate concentration, causes wound damage and at much higher concentration 25% is toxic.

However, the dental care composition as disclosed in the present invention uses much lower concentrations of sodium perborate, wherein at such optimal concentration it acts as oxidising agent providing anti-inflammatory, anti-septic and anti-oxidant properties.

In the above mentioned embodiment, the concentration of sodium perborate in the present invention is less than 0.2% or in other words the concentration of sodium perborate is less than 2 mg/ml more specifically 1 mg/ml.

In yet another embodiment, the anti-microbial, anti-septic and anti-inflammatory agent of the novel composition is honey due to its structure made up of hydrogen peroxide and gluconic acid. The said agent is a natural sweetener and when used in the formulation acts as a natural anti-microbial agent with its high osmolarity, acidity (low pH), and ratio of hydrogen peroxide and non-hydrogen peroxide components. The honey used in the present formulation when diluted generate hydrogen peroxide due to the activation of the enzyme glucose oxidase. Glucose oxidase oxidise glucose to gluconic acid and hydrogen peroxide which induces the anti-microbial effect in the present formulation.

In the above mentioned embodiment, the concentration of honey used in dental care composition is less than 0.5% specially, less than 0.2%.

In one embodiment, the synergistic effect of the composition is achieved, wherein the active oxygen from the oxidising agent sodium perborate, triggers the anti-bacterial activity in the honey, triggers the anti-oxidant and anti-inflammatory properties of guava leaf extract, to removes bacterial plaques or dental stains in the oral cavity and reduce oral inflammation.

In one embodiment, the present invention provides one or more benefits comprising and not limiting to post implant care for enhanced healing, reduces attachment of bacterial plaque, protection of oral soft tissues, reduced peri-implantitis disease (inflammation of the gum and bone structure around a dental implant), improved cosmetic property such as teeth whitening, and maintaining optimal antioxidant level in the saliva to retain moisture of the tissue in the oral cavity.

In an embodiment, the invention discloses a novel dental care composition comprising combination of guava leaf extract, honey and sodium perborate wherein the composition exhibits anti-oxidant, anti-bacterial, anti-inflammatory and anti-septic properties.

In the above mentioned embodiment, the concentration of guava leaf extract is 5%, the concentration of honey is 0.1% and the concentration of sodium perborate is 0.1%.

In one embodiment, the present invention is a carefully formulated synergistic formulation, wherein the composition and ratio of the oxidising agent, anti-microbial agent and the anti-oxidant agent are formulated such that the combination of the said agents provide higher anti-inflammatory, anti-bacterial, astringent tissue repair and plaque removal activity compared to the independent effect of the same. Furthermore, the Vitamin C present in the present composition prevents the dryness of the mouth due to various medications and aids in restoring the salivary balance in the oral cavity.

Figure 1:
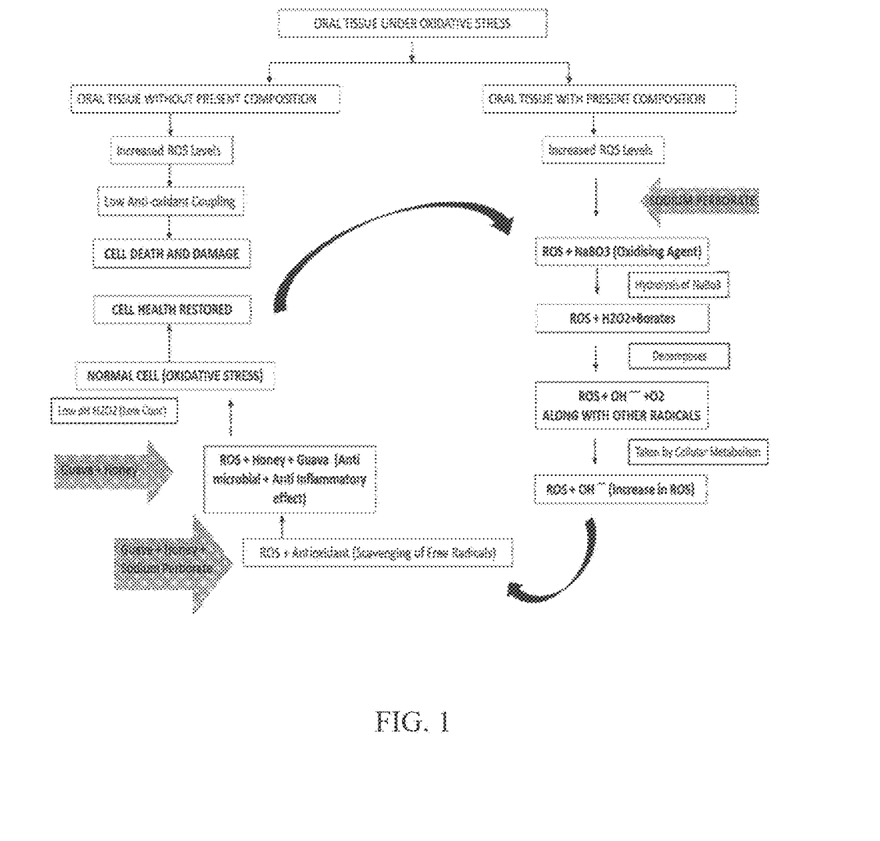
FIG. 1. Schematic representation of cellular metabolism of oral issue under oxidative stress with the composition of the present invention.

In one embodiment, as in FIG. 1, the present invention when administered into an oral cavity, which under oxidative stress exhibits elevated levels of ROS (Reactive Oxygen Species). This elevated ROS triggers the activation of Sodium Perborate in the said composition, whereby Sodium perborate hydrolyses to produce hydrogen peroxide and other ions. With the increase in this free radicals and other ions, the anti-oxidant from the guava leaf extract (Radical scavenging) combines with the free radicals and reduces the oxidative stress. Furthermore, honey present in the composition comprises hydrogen peroxide and gluconic acid acting in synergy as a potent immunomodulatory and anti-inflammatory agent. Furthermore, the low acidic pH of honey acts as a bacteriostatic agent. The said composition when administered in the oral cavity acting in synergy restore normal cell health and healthy oral cavity.

In an embodiment, the invention discloses a method of treating periodontal disease condition comprising administration of a novel dental care composition comprising 5% guava leaf extract, 0.1% honey and 0.1% Sodium perborate synergistically interacts when introduced in the oral environment to act on cells under oxidative stress, providing wound healing via anti-oxidant, anti-inflammatory and anti-microbial activities.

In yet another embodiment the invention discloses, a method of treating gingivitis in a patient comprising administration of a dental care composition comprising combination of guava leaf extract, honey and sodium perborate.

In an another embodiment the invention discloses, a method of treating ulcerative gingivitis in a patient comprising administration of a dental care composition comprising combination of guava leaf extract, honey and sodium perborate.

In an embodiment the invention discloses, a method of treating peri-implantitis in a patient comprising administration of a dental care composition comprising combination of guava leaf extract, honey and sodium perborate.

In yet another embodiment, the invention discloses a method of treating peri-implant mucositis in a patient comprising administration of a dental care composition comprising combination of guava leaf extract, honey and sodium perborate.

In an embodiment, the invention discloses a novel dental care composition comprising combination of 5% guava leaf extract, 0.1% honey and 0.1% sodium perborate wherein the composition is effective in treatment of gingivitis, ulcerative gingivitis, peri-implantitis and per-implant mucositis.

In any of the above mentioned embodiments, inflammation in soft tissues of periodonatal disease condition is reduced observed within 3 days to one week.

In an embodiment, the invention discloses a novel dental care composition comprising
   5% guava Extract (5%)
   0.1% processed honey (0.1%)
   0.1% sodium perborate monohydrate
   13% glycerine
   5% zemea (5%)
   1% cremaphore RH-40 (1%)
   0.008% guava Flavour (0.008%)
   0.01% Cooling Flavour B (0.01%
   75.78% water.

In the above mentioned embodiments, the dental care composition is effective in adults to treat various dental infections.

In an embodiment, the novel dental care composition as disclosed in the invention is effective in treatment of gingivitis, ulcerative gingivitis, per-implantitis and pen-implant mucositis wherein improvement in the condition in terms of reduction in inflammation of the soft tissue is from 3 days to 3 weeks upon usage of the said composition depending upon the severity of the disease condition.

In one embodiment, the formulation of the present invention, when administered to the oral cavity in oxidative stress, wherein the levels of Reactive Oxygen Species (ROS) are elevated. This elevated level of ROS triggers the Sodium Perborate due to its Reduction-Oxidation property which further hydrolyses to hydrogen peroxide and other ions.

In yet another embodiment, the formulation of the present invention when administered to the oral cavity in oxidative stress provides the anti-oxidants from guava extract acts as the free radical scavenger and reacts to render all free radicals harmless thus reducing the oxidative stress.

In yet another embodiment, the formulation of the present invention when administered to the oral cavity provide the anti-bacterial, aseptic and anti-inflammatory agent honey made up of hydrogen peroxide and gluconic acid. The low pH of the gluconic acid and high concentration provides the requisite bacteriostatic environment in the oral cavity. Furthermore, the hygroscopic nature of honey absorbs water from the surface and osmolality changes causing anti-bacterial effect. Additionally, hydrogen peroxide of honey causes oxidation of glucose to gluconic acid thus acting as a potent immunomodulatory and anti-inflammatory agent.

In one embodiment, the present invention relates to the use of said novel synergistic composition, wherein the composition is administered as such as toothpaste (dentifrice), prophylactic paste, tooth powder, tooth polish, tooth gel, chewing gum, candy, lozenge, mouthwash, mouth sprays (for more specific application to tobacco users), and/or gel for local delivery in the gum pockets or the like.

In yet another embodiment, the present invention provides a synergistic composition that provides optimum concentration of antioxidant that restores the balance in the oral cavity to aid in tissue repair and prevent any further damage of the same. Advantageously, the synergistic composition provides a unique combination of ingredients that address majority of issues in the oral cavity such as increased oxidative stress caused due to unhealthy food/lifestyle habits including alcohol, smoking chewing tobacco, and salivary dryness caused due to medication especially in adults etc. Furthermore, the antibacterial agents and anti-inflammatory agent protect the oral cavity against infections and reduces the mineral deposits in teeth providing its cosmetic properties.

In any of the above mentioned embodiments, the novel dental care composition as disclosed in the present invention is free of chemical anti-septic agents such as sodium hypochlorite, chlorhexidine and EDTA. The chemical anti-septic agents induces growth of resistance bacteria.

In any of the above mentioned embodiments, the novel dental care composition additionally comprising, flavouring agent, cooling agent, colouring agent and humectant.

In one embodiment, the unique formulation of the present invention addresses the balance in ROS (Reactive oxygen Species) by providing a balance in normal physiological role to help maintain healthy gums and oral mucosal tissue and the oxidative stress of oral cavity to prevent further damage.

The disclosed novel dental care compositions are effective in treatment of various dental disease and the said composition does not decrease the production of saliva.

EXAMPLES

The present invention may be better understood through to the following examples. These examples are included to describe exemplary embodiments only and should not be interpreted to encompass the entire breadth of the invention.

Example 1

Preparation of Dental Care Composition

The dental care composition as disclosed in the invention was prepared by following process purified water was taken in a container to which glycerin was added and mixed thoroughly, post which zemea was added followed by addition of guava leaf extract and honey and the obtained mixture was mixed thoroughly. Sodium perborate was dissolved in water and was added to the above mixture and mixed continuously. Post which, coloring agent Cremaphore-RH40, flavoring agent Guava flavor, and cooling flavor B was added to the above mixture. All the concentrations of various agents were adjusted to get the dental care composition. Details of the composition is given in below Table 1.

TABLE 1

Dental care composition prepared as per example 1.

| S. No | Ingredients | Quantity in percentages (%) |
|---|---|---|
| 1 | Glycerin | 13.0 |
| 2 | Guava Extract | 5.00 |
| 3 | Processed honey | 0.10 |
| 4 | Cremaphore RH-40 | 1.00 |
| 5 | Guava Flavour | 0.008 |
| 6 | Cooling Flavour B | 0.01 |
| 7 | Sodium perborate monohydrate | 0.10 |
| 8 | Zemea | 5.00 |
| 9 | Purified water | 75.78 |

Example 2

Anti-Oxidant Properties of Components Present in Dental Care Composition

To assess anti-oxidant properties of various therapeutic/active components present in dental care composition, various concentrations of guava leaf extract (5%, 10%, 15% and 20%), honey (0.1%, 0.2%, 0.3% and 0.4%) and sodium perborate 0.01%, 0.1%, 0.2%, 0.3% and 0.4%) were prepared. At the same time, the combination of these components was also prepared as another composition. All these compositions were subjected anti-oxidant/radical scavenging activity assay using 2,20-azinobis-3-ethylbenzothiazoline-6-sulfonic acid (ABTS) assay.

ABTS assay was conducted by incubating various concentration of compositions prepared above with 3 ml of 7 mM ABTS solution and 100 mM potassium persulfate solution in methanol at room temperature for 30 minutes and then absorbance was measured at 734 nm using spectrophotometer (King lab). 7 mM ABTS and 100 mM potassium persulfate solution in methanol was used as control in this experiment. Lower absorbance of the reaction mixture indicated higher free radical scavenging activity. The percentage of the ABTS radical scavenging is calculated using the equation as given below:

Radical scavenging activity (%)=(Abs control($A0$)−Abs sample($A1$)/Abs control($A0$))×100.

where A0 is the absorbance of the control, and A1 is the absorbance of the composition.

The results of scavenging activity of various compositions are given in below Table 2.

TABLE 2 radical scavenging activity of various compositions measured using ABTS assay.

| S. No | Composition | Radical Scavenging activity (%) |
|---|---|---|
| 1 | Control | 0 |
| 2 | 5% Guava leaf extract | 25.18 |
| 3 | 10% Guava leaf extract | 58.99 |
| 5 | 15% Guava leaf extract | 83.58 |
| 6 | 0.1% honey | 4.63 |
| 7 | 0.2% Honey | 8.13 |
| 8 | 0.3% honey | 10.46 |
| 9 | 0.01% sodium perborate | 69.38 |
| 10 | 0.1% sodium perborate | 90.02 |
| 11 | 0.2% sodium perborate | 91.19 |
| 12 | 0.3% sodium perborate | 92.37 |
| 13 | 5% guava leaf extract + 0.1% honey + 0.1% sodium perborate | 94.88 |

Example 3

Anti-Microbial Property of Dental Care Composition

To assess anti-microbial property of dental care composition as disclosed in examples, first the sample was incubated with a prescribed inoculum of various microorganisms including Bacteria and Fungi at a particular temperature and the samples were withdrawn at particular time intervals and checked the organism present in the sample.

In this experiment, first inoculum was prepared by transferring bacteria (*Staphylococcus aureus* ATCC6538, *E. coli* ATCC8739, *Pseudomonas aeruginosa* ATCC 9027) to soya bean casein digest gar (SCDA) media and incubated at 32.5±2.5° C. for 24 hours on SCDA.

Yeast (*Candida albicans* ATCC 10231) 22.5±2.5° C. was transferred to sabouraud dextrose agar (SDA) and incubated at 22.5±2.5° C. for 24 hours on SDA.

Fungi (*Aspergillus brasilliensis* ATCC 16404) was incubated at 22.5±2.5° C. for 3 days on SDA.

*Streptococcus pyrogenes* ATCC 19615 was transferred on to non-selective sheep blood agar at 35° C. to 37° C. and incubated in aerobic atmosphere for 48 hours.

*Lactobacillus acidophilus* ATCC 4356 was transferred to MRS (Man, Rogasa Sharpe) agar and incubated at 35° C. to 37° C. in aerobic atmosphere for 48 hours.

After incubation, all the cultures were washed with 10 ml sterile solution having pH of 7.2. Post which, the culture was scrapped with a sterile loop, transfer the washed solution into a clean sterile tube and vortex before use. From the washed solution, 10 fold serial dilution was carried out using sterile saline solution.

20 ml of the dental care composition as disclosed in example 1 was transferred to bacteriological containers and was inoculated with standardized inoculum (0.5%-0.1% ($1*10^5$ or $1*10^6$ cfu per ml/gm of product)) and were mixed thoroughly for even distribution of surviving cells. To maintain control in this experiment, standardized inoculum was inoculated in normal saline solution. Pour plates were prepared for all the samples including control using SCDA for bacteria, SDA for yeast, and moulds for fungi. Bacteria was incubated at 30° C. to 35° C. for 72 hours, yeast at 20° C. to 25° C. for 3 days, and moulds at 20° C.-25° C. for 5 days. For *Streptococcus pyrogenes* was incubated at 35° C.-37° C. for 72 hours. For *Lactobacillus acidophilus* was incubated in MRS agar at 35° C. to 37° C. in aerobic atmosphere for 72 hours. The inoculated containers were incubated at 20° C. to 25° C. and were examined after 48 hours, 7 days, 14 days, 21 days and 28 days subsequent to inoculation and the number viable organisms were counted at different time intervals and the log reduction was calculated. Results of the dental care composition for different organisms are given in below Table 3(a) for bacteria and Table 3 (b) for yeast and Fungi.

TABLE 3(a)

Log10 reduction of various bacteria's when incubated with the dental care composition as disclosed in Example 1.

| Microorganisms | Intervals & observed cfu [Plate] | | | | | | | |
|---|---|---|---|---|---|---|---|---|
| | 48 Hrs | | 7$^{th}$ day | | 14$^{th}$ day | | 28$^{th}$ day | |
| | Observed | Log$^{10}$ reduction | Observed | Log$^{10}$ reduction | Observed | Log$^{10}$ reduction | Observed | Log$^{10}$ reduction |
| *Staphylococcus aureus* | Nil | >5.86 | Nil | >5.86 | Nil | >5.86 | Nil | >5.86 |
| *Pseudomonas aeruginosa* | Nil | >5.91 | Nil | >5.91 | Nil | >5.91 | Nil | >5.91 |
| *Escherichia coli* | Nil | >5.92 | Nil | >5.92 | Nil | >5.92 | Nil | >5.92 |
| *Streptococcus Pyogenes* | Nil | >5.89 | Nil | >5.89 | Nil | >5.89 | Nil | >5.89 |
| *Lactobacillus acidophilus* | Nil | >5.84 | Nil | >5.84 | Nil | >5.84 | Nil | >5.84 |

TABLE 3(b)

Log10 reduction of yeast and moulds when incubated with the dental care composition as disclosed in Example 1.

| Microorganisms | Intervals & observed cfu [Plate] | | | |
|---|---|---|---|---|
| | 14$^{th}$ day | | 28$^{th}$ day | |
| | Observed | Log$_{10}$ reduction | Observed | Log$_{10}$ reduction |
| *Candida albicans* | Nil | >5.79 | Nil | >5.79 |
| *Aspergillus brasilansis* | Nil | >4.46 | Nil | >4.46 |

Example 4: Treatment of Gingivitis

Gingivitis means inflammation of the gums, or gingiva. It commonly occurs because a film of plaque, or bacteria, accumulates on the teeth. Gingivitis is a non-destructive type of periodontal disease, but untreated gingivitis can progress to periodontitis. A variety of patients who had indications of gingivitis was treated with dental care composition as prepared and disclosed in the example 1. Improvement in the condition was seen within 1 week.

Figure 2A:
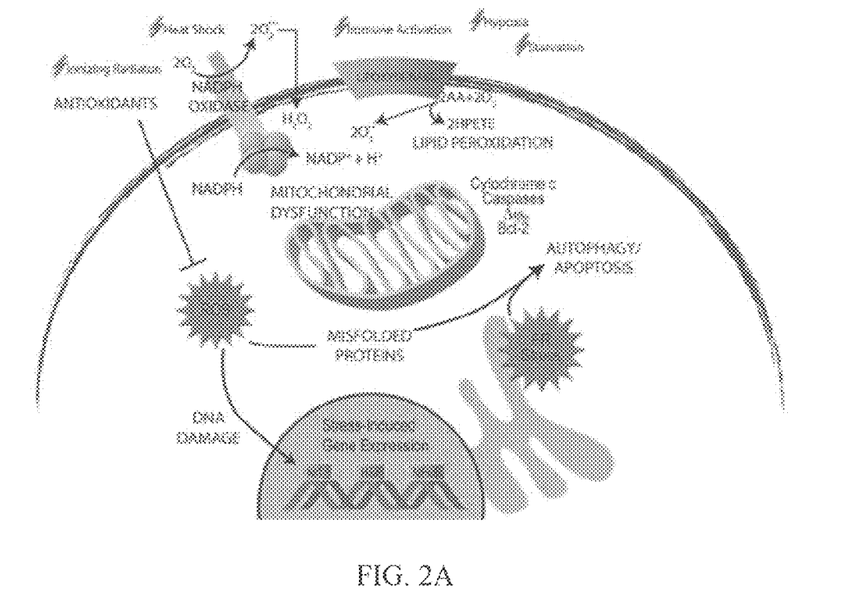
FIG. 2. Shows images of mechanism of action of antioxidants obtained with the dental care composition of the present invention. (a)—Cell in Oxidative stress (b) Scavenging by antioxidant (c) Reaction initiated when Honey is coupled with ROS.
Figure 2B:
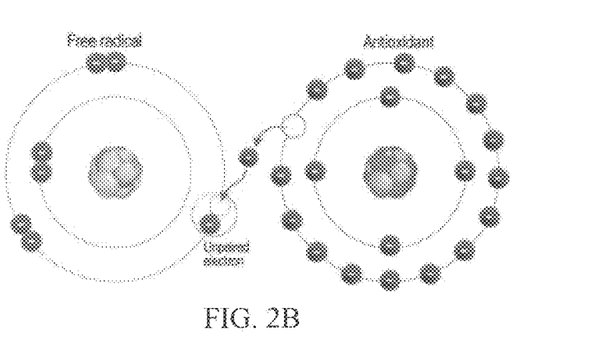
Figure 2C:
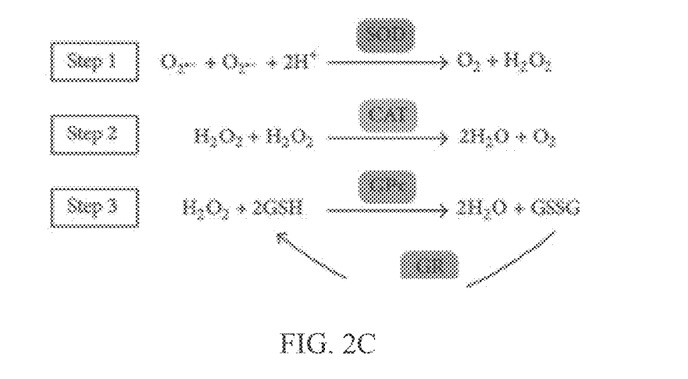
Figure 3A:
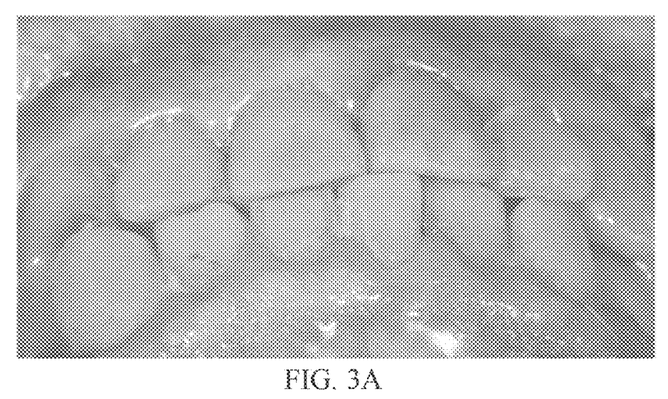
FIG. 3. Shows images of before (a) and after (b) treatment for a patient having gingivitis with dental care composition as disclosed in example 4 of the present invention.
Figure 3B:
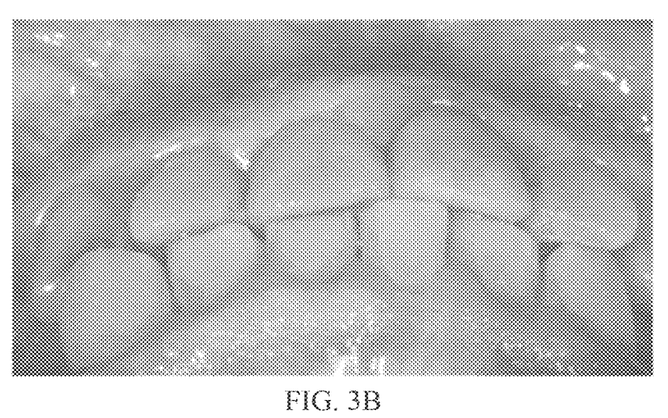

One of the patients was a male, 40 years old used the disclosed dental care composition as mouth wash twice daily and felt relief from gingivitis in 3 days (results before and after given in FIGS. 2 (*a*) and (*b*)). Another patient who was also a male, 45 years had severe gingivitis used the dental composition thrice a day and observed better results after 3 weeks (results before and after given in FIGS. 3 (*a*) and (*b*).

Example 5: Treatment of Ulcerative Gingivitis

Ulcerative gingivitis is trench mouth, a progressive painful infection with ulceration, swelling and sloughing off of dead tissue from the mouth and throat due to the spread of infection from the gums. A patient who had indications of ulcerative gingivitis was treated with dental care composition as prepared and disclosed in the example 1. Improvement in the condition was seen within 1 week.

Figure 4A:
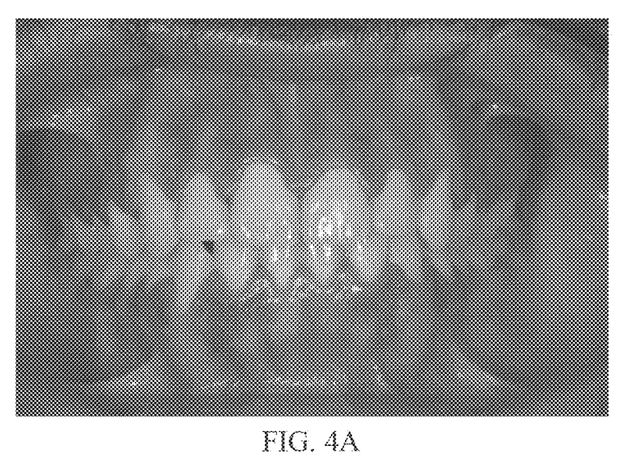
FIG. 4. Shows images of before (a) and after (b) treatment for a patient having gingivitis with dental care composition as disclosed in example 4 of the present invention.
Figure 4B:
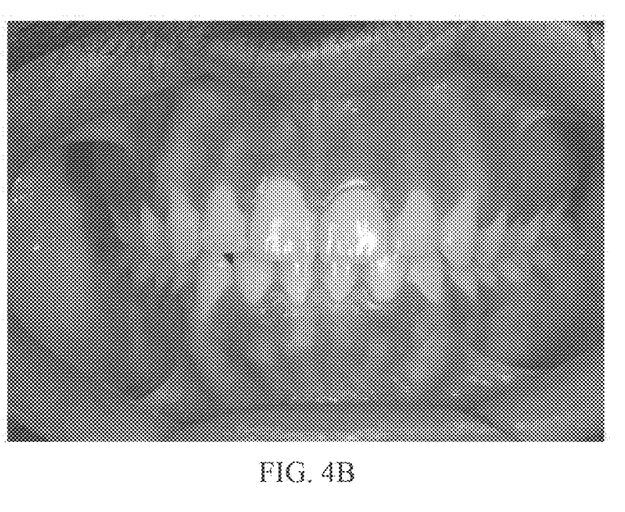

The patient was a male, 50 years old used mouth wash twice daily and felt relief from ulcerative gingivitis in one week (results before and after given in FIGS. 4 (*a*) and (*b*)).

Example 6: Treatment of Peri Implantitis

Peri implantitis is an infectious disease that causes inflammation of the gum and the bone structure around a dental implant. Chronic inflammation causes bone loss, which can lead to a loose implant that eventually could fall out. A patient who had indications of peri implantitis was treated with dental care composition as prepared and disclosed in the example 1. Improvement in the condition (inflammation of soft tissue) was seen within 1 week.

Figure 5A:
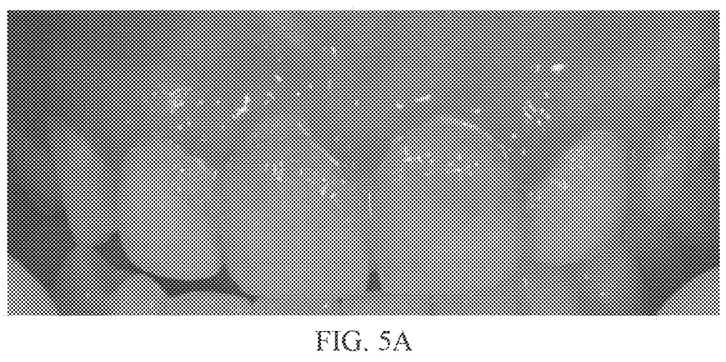
FIG. 5. Shows images of before (a) and after (b) treatment for a patient having ulcerative gingivitis with dental care composition as disclosed in example 5 of the present invention.
Figure 5B:
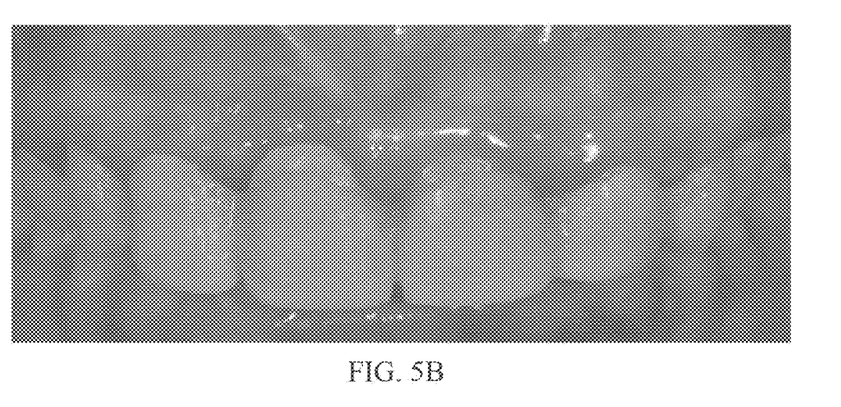

The patient was a male, 53 years old who had implant from the last 4-5 years used mouth wash twice daily and felt relief from inflammation of the soft tissue in one week (results before and after given in FIGS. 5 (*a*) and (*b*)). The patient was further advised with antibiotic treatment and surgical intervention based on the requirement of the case to treat Peri-implantitis.

Example 7: Treatment of Peri Implant-Mucositis

Peri-implant mucositis is an inflammatory lesion of the soft tissues surrounding an endosseous implant in the absence of loss of supporting bone or continuing marginal bone loss. A patient who had indications of peri implant-mucositis was treated with dental care composition as prepared and disclosed in the example 1. Improvement in the condition (inflammation of soft tissue) was seen within 1 week.

Figure 6A:
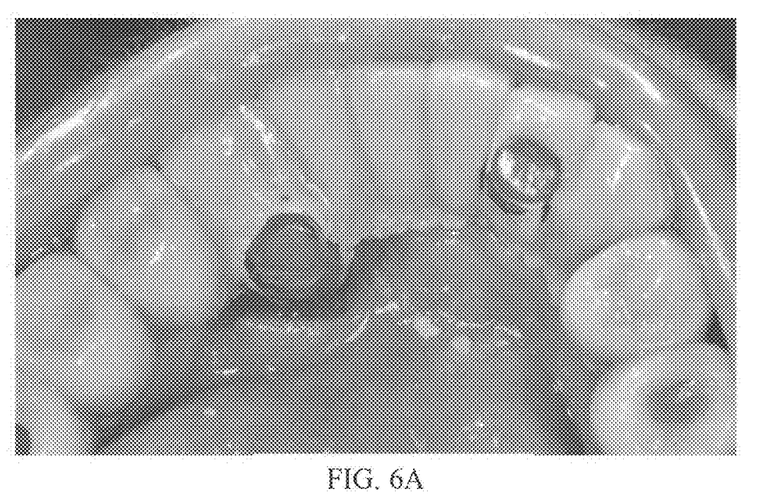
FIG. 6. Shows images of before (a) and after (b) treatment for a patient having peri-implantitis with dental care composition as disclosed in example 6 of the present invention.
Figure 6B:
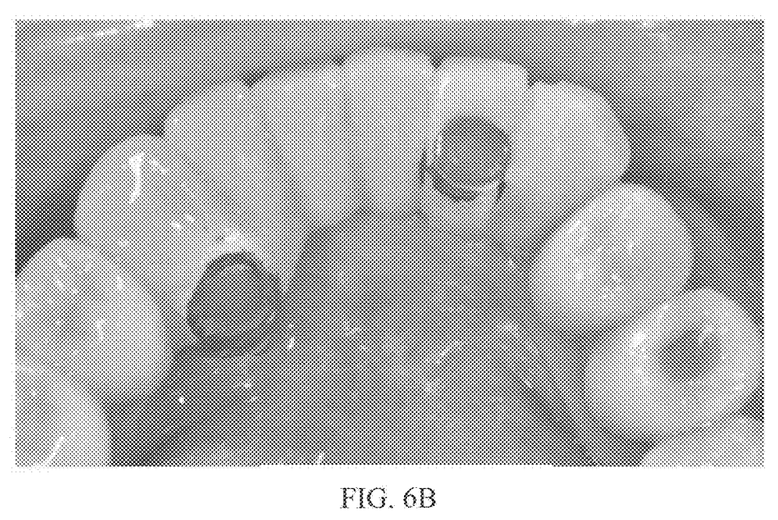
Figure 7A:
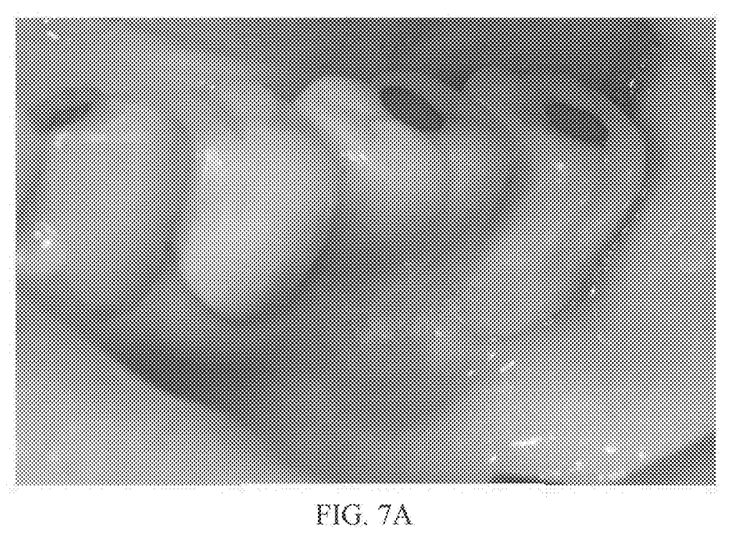
FIG. 7. Shows images of before (A) and after (B) treatment for a patient having per-implant mucositis with dental care composition as disclosed in example 7 of the present invention.
Figure 7B:
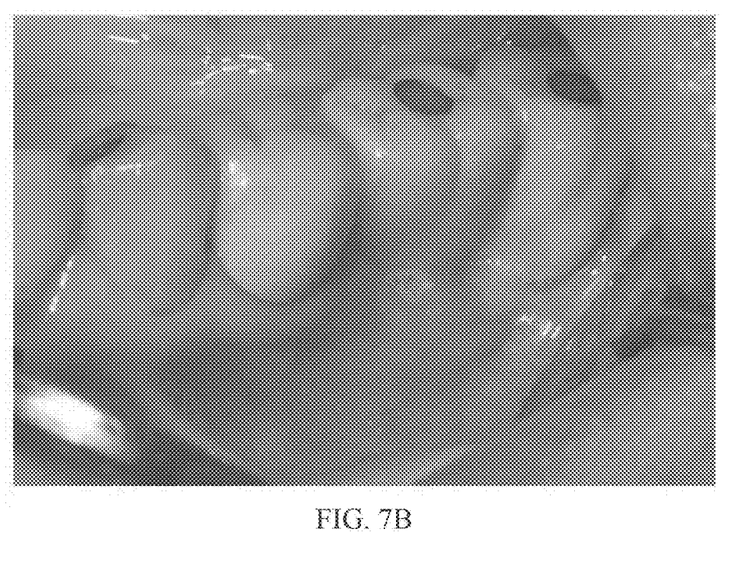

The patient was a male, 45 years old who had implant from the last 4-5 years used mouth wash twice daily and felt relief from pen-implant mucositis in two week (results before and after given in FIGS. 6 (*a*) and (*b*). The patient was further advised with antibiotic treatment and surgical intervention based on the requirement of the case to treat Pen-implant musocistis.

None of the patients who had gingivitis or ulcerative gingivitis or peri-implantitis or peri implant mucositis felt dryness of the mouth after using dental care composition of the present invention.

The invention claimed is:

1. A dental care composition comprising: 5% guava leaf extract, 0.1% honey, and 0.1% sodium perborate: wherein the guava lead extract, honey, and sodium perborate synergistically interact when introduced in the oral environment to act on cells under oxidative stress, thereby providing wound healing via anti-oxidant, anti-inflammatory and anti-microbial activities.

2. The dental care composition of claim 1, wherein the dental care composition is an effective treatment for various dental diseases.

3. A method of treating periodontal disease conditions, the method comprising: administration of a dental care composition comprising 5% guava leaf extract, 0.1% honey, and 0.1% sodium perborate, wherein the guava leaf extract, honey, and sodium perborate synergistically interact when introduced into the oral environment to act on cells under oxidative stress, thereby providing wound healing via anti-oxidant, anti-inflammatory and anti-microbial activities.

4. The method of claim 3, wherein the method is used to treat the following periodontal disease conditions: gingivitis, ulcerative gingivitis, peri-implantitis, and per-implant mucositis.

* * * * *